(12) United States Patent
Maurin

(10) Patent No.: US 8,208,016 B2
(45) Date of Patent: Jun. 26, 2012

(54) AUTOMATED VISUAL CHECKING DEVICE

(75) Inventor: Denis Maurin, Le Barp (FR)

(73) Assignee: Proditec, Pessac (FR)

( * ) Notice: Subject to any disclaimer, the term of this patent is extended or adjusted under 35 U.S.C. 154(b) by 470 days.

(21) Appl. No.: 12/593,157

(22) PCT Filed: Mar. 21, 2008

(86) PCT No.: PCT/FR2008/050493
§ 371 (c)(1), (2), (4) Date: Sep. 25, 2009

(87) PCT Pub. No.: WO2008/132389
PCT Pub. Date: Nov. 6, 2008

(65) Prior Publication Data
US 2010/0118134 A1 May 13, 2010

(30) Foreign Application Priority Data

Mar. 26, 2007 (FR) ........................................ 0754027

(51) Int. Cl.
*H04N 7/18* (2006.01)
*G06F 15/16* (2006.01)
(52) U.S. Cl. ........................................................ 348/86
(58) Field of Classification Search ............... 348/86–89
See application file for complete search history.

(56) References Cited

U.S. PATENT DOCUMENTS

| 5,286,980 A | 2/1994 | Richert |
| 2002/0109094 A1 | 8/2002 | Goetz et al. |

FOREIGN PATENT DOCUMENTS

| JP | 02/092168 | 3/1990 |
| JP | 2001-208520 | 8/2001 |

OTHER PUBLICATIONS

International Search Report dated Sep. 18, 2008, from corresponding PCT application.

*Primary Examiner* — Zarni Maung
(74) *Attorney, Agent, or Firm* — Young & Thompson

(57) ABSTRACT

A device (24) for automated visual monitoring of products, in particular products of elongated shape, having at least one longitudinal axis (10) and advancing essentially continuously in a direction A that is essentially parallel to their longitudinal axis (10), whereby guiding elements (26) keep the products during their passage in the field C by visual monitoring elements (28), the automated visual monitoring device (24) being characterized in that the guiding elements (26) include at least one slot (34) that is aligned with at least one reflective surface (32) that is arranged in the field C of the visual monitoring elements (28) behind the site of passage of the products.

16 Claims, 5 Drawing Sheets

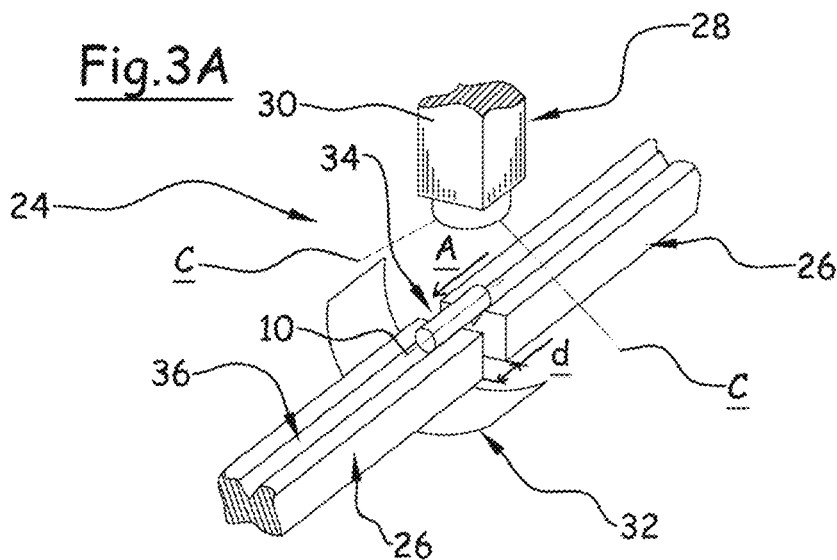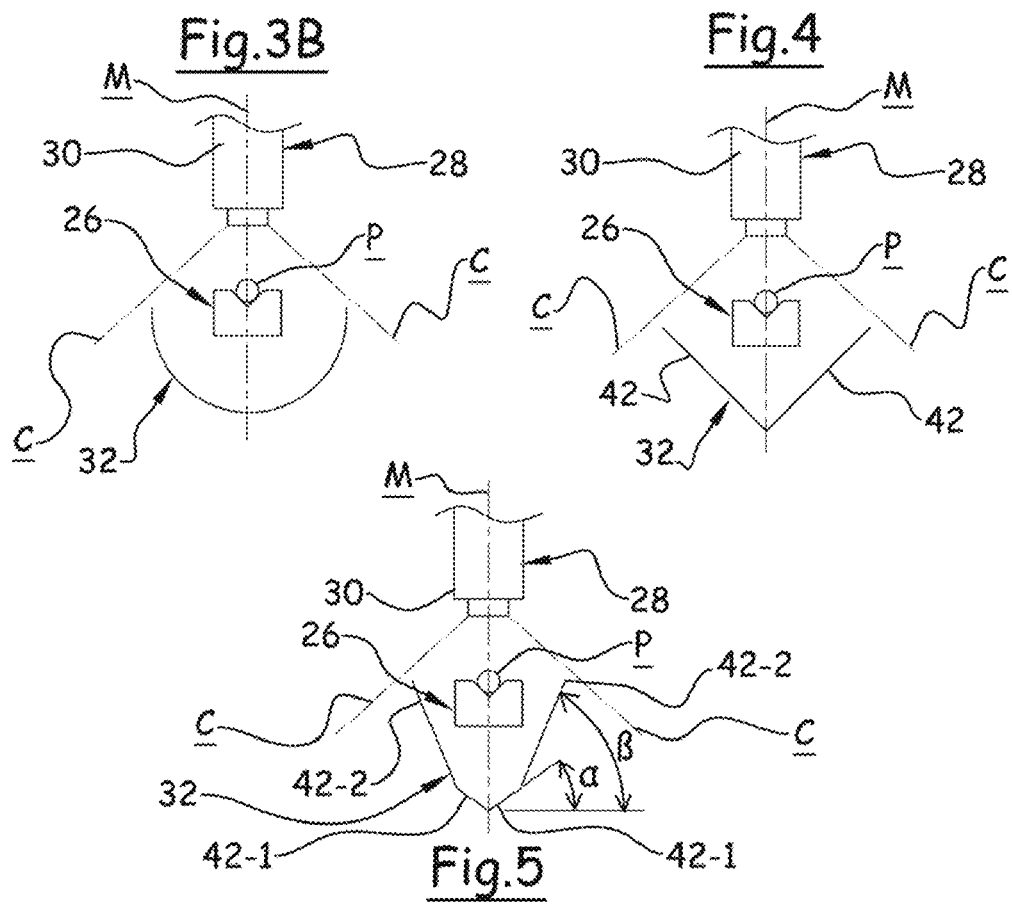

AUTOMATED VISUAL CHECKING DEVICE

Figure 1:
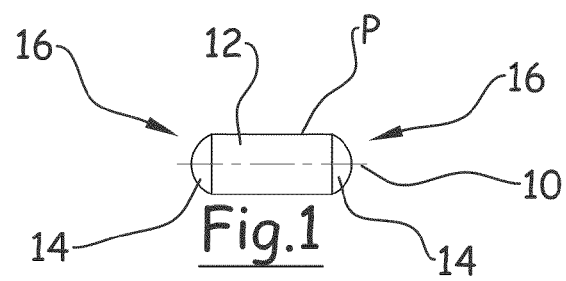

This invention relates to a device for automated visual monitoring, more particularly to a device that makes possible the monitoring of the entire outside longitudinal wall of a product of elongated shape.

In numerous industries: plastic and rubber, pharmaceuticals, metallurgy, automobile, . . . the monitoring systems use state-of-the-art technologies to monitor the quality of products and to reject products that have defects.

Among the various types of monitoring that can be implemented, visual monitoring is industrially advantageous because it involves non-destructive monitoring.

The visual monitoring device, object of this invention, is thus to make it possible to verify the quality of all of the products of a manufacturing lot and not to be limited to statistical monitoring of several samples of products taken in said manufacturing lot.

The quality control is quite often the ultimate verification stage of products before packaging and shipping to clients. It is therefore necessary that the monitoring be carried out with the greatest exactness so as to reject all of the products that do not meet the quality criteria that are imposed.

In addition, whereby production rates increase uniformly by means of the optimization of production means and the continuous improvement of the production processes, it is inconceivable that the output of a production chain be limited by the visual monitoring device located in said chain.

Manufacturers, in particular those of the pharmaceutical sector, are looking for visual monitoring devices that can meet the requirements of their specifications that relate in particular to the high production rates and to a high monitoring reliability of the quality of the products of each manufacturing lot.

The automation of visual monitoring is a solution that makes it possible today to produce visual monitoring devices that can track the increase in production rates while ensuring reliable monitoring of the products in series and their rejection, if necessary.

So as to be able to be inspected in series, the products that are obtained from a manufacturing lot generally advance in the field of means of visual monitoring using guiding means that make it possible to make them advance in an essentially continuous manner.

During the passage of each product of a manufacturing lot in the field of visual monitoring means, an automated visual monitoring device is to make it possible to inspect the entire outside surface of the product without which the visual monitoring would not be complete.

Numerous devices have been designed to make possible the inspection of the entire outside surface of a product during its passage into the field of the visual monitoring means; however, these devices generally multiply the visual monitoring means, such as a camera, and/or the means for changing the orientation of said product.

The design of an automated visual monitoring device is directly connected to the shapes of the products to be inspected and to the quality criteria imposed.

The invention pays particular attention to the inspection of products P of elongated shape, i.e., at least as long as wide, having at least one longitudinal axis 10 that is central, whereby said products P advance in a direction that is essentially parallel to their longitudinal axis 10.

The longitudinal axis 10 is considered to be central when it passes essentially through the center of any section that is carried out in said product P of elongated shape.

Even more specifically, the invention relates to the inspection of the entire outside longitudinal wall 12 of a product P, i.e., the wall that connects the two surfaces 14 that are located at each end 16 of a product P.

Each surface 14 that is located at one of the ends 16 of a product P can be flat, bent, hemispherical, hollow or any other shape.

The invention is not concerned with the inspection of said surfaces 14 located at the ends of a product P of elongated shape; it can easily be used with means that are known to one skilled in the art.

By contrast, the inspection of the entire outside longitudinal wall 12 of products P of elongated shape is more difficult to carry out, in particular in the case that is relative to this invention where said products P of elongated shape advance quickly and essentially continuously to track the production rates imposed upstream from the manufacturing chain, several tens per second to provide a connection.

Figure 2A:
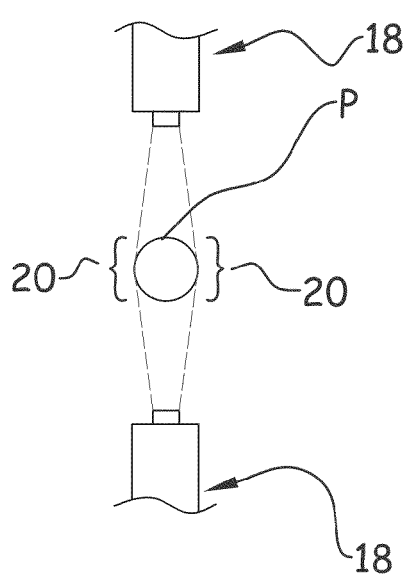

A first design of the prior art, illustrated in FIG. 2A, to inspect the entire outside longitudinal wall 12 of products P of elongated shape consists in advancing said products P essentially continuously in the field of visual monitoring means 18, in particular two cameras arranged face to face and between which passes the product P to be inspected. This first design of the prior art makes it possible to inspect a product P starting from only two images.

This first solution does not allow an optimum inspection of the entire outside longitudinal wall 12 of the products P. Actually, the wall 12 of a product P can have zones 20 that are too tilted to be suitable in the field of visual monitoring means 18 and therefore to be inspected correctly starting from only two views of said product.

Figure 2B:
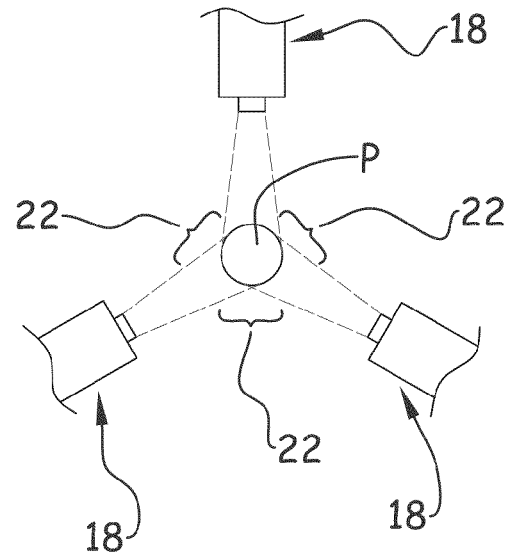

A second design of the prior art, illustrated in FIG. 2B, proposes using three cameras at about 120 degrees each from one another to allow the inspection of the entire outside longitudinal wall 12 of products P of elongated shape. This arrangement makes it possible to create cover zones 22 that make it possible to correctly inspect the entire outside longitudinal wall 12 of a product P from three views of said product.

However, this second design of the prior art has the major drawback of requiring three cameras, complicating the monitoring device and multiplying the costs of production and maintenance as well as the risks of failure.

According to a third design of the prior art, in particular used in the device that is described in the patent JP-02092168, the product to be monitored is rotated so as to allow the inspection of its entire outside wall.

For an industrial application, in particular an application with a manufacturing chain of pharmaceutical products, it is taken into consideration that a monitoring of products P in movement and advancing without precise guiding means can reduce the reliability of said monitoring as well as the rate of inspected products.

Consequently, this invention does not relate to the devices or processes of automated visual monitoring according to which the products P are not kept during their passage in the field of visual monitoring means.

Also, the purpose of this invention is to eliminate the drawbacks of the prior art by proposing an automated visual monitoring device that makes possible the inspection of the entire outside longitudinal wall of products of elongated shape, whereby said products are kept during their passage in the field of visual monitoring means and the visual monitoring means used for this purpose are limited to only one camera.

For this purpose, the object of the invention is a device for automated visual monitoring of products P, in particular products of elongated shape, having at least one longitudinal axis and advancing essentially continuously in a direction that is essentially parallel to their longitudinal axis, whereby guiding means keep the products P during their passage in the field of visual monitoring means, and whereby said automated visual monitoring device is characterized in that the guiding means, keeping the products P essentially immobile during the visual monitoring, comprise at least one slot that is aligned with at least one reflective surface that is arranged in the field of visual monitoring means behind the site of passage of the products P.

Figure 6:
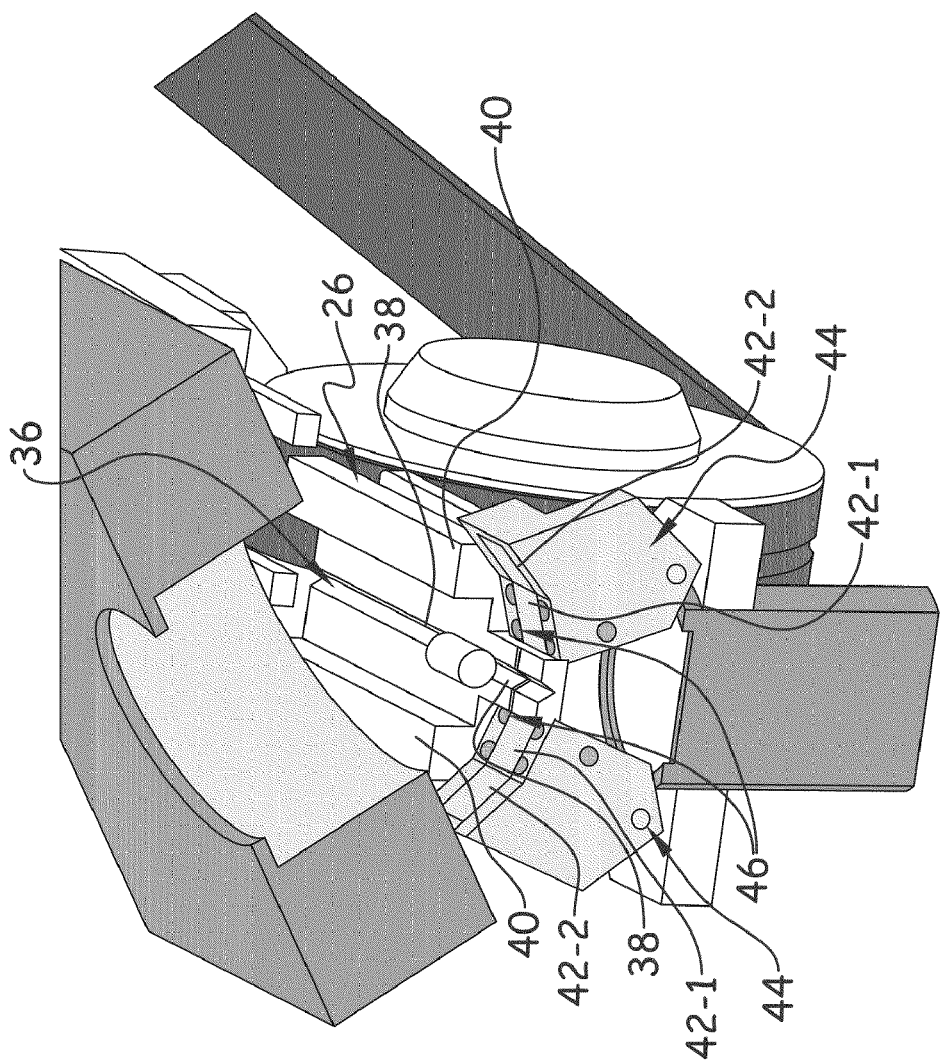
Figure 7:
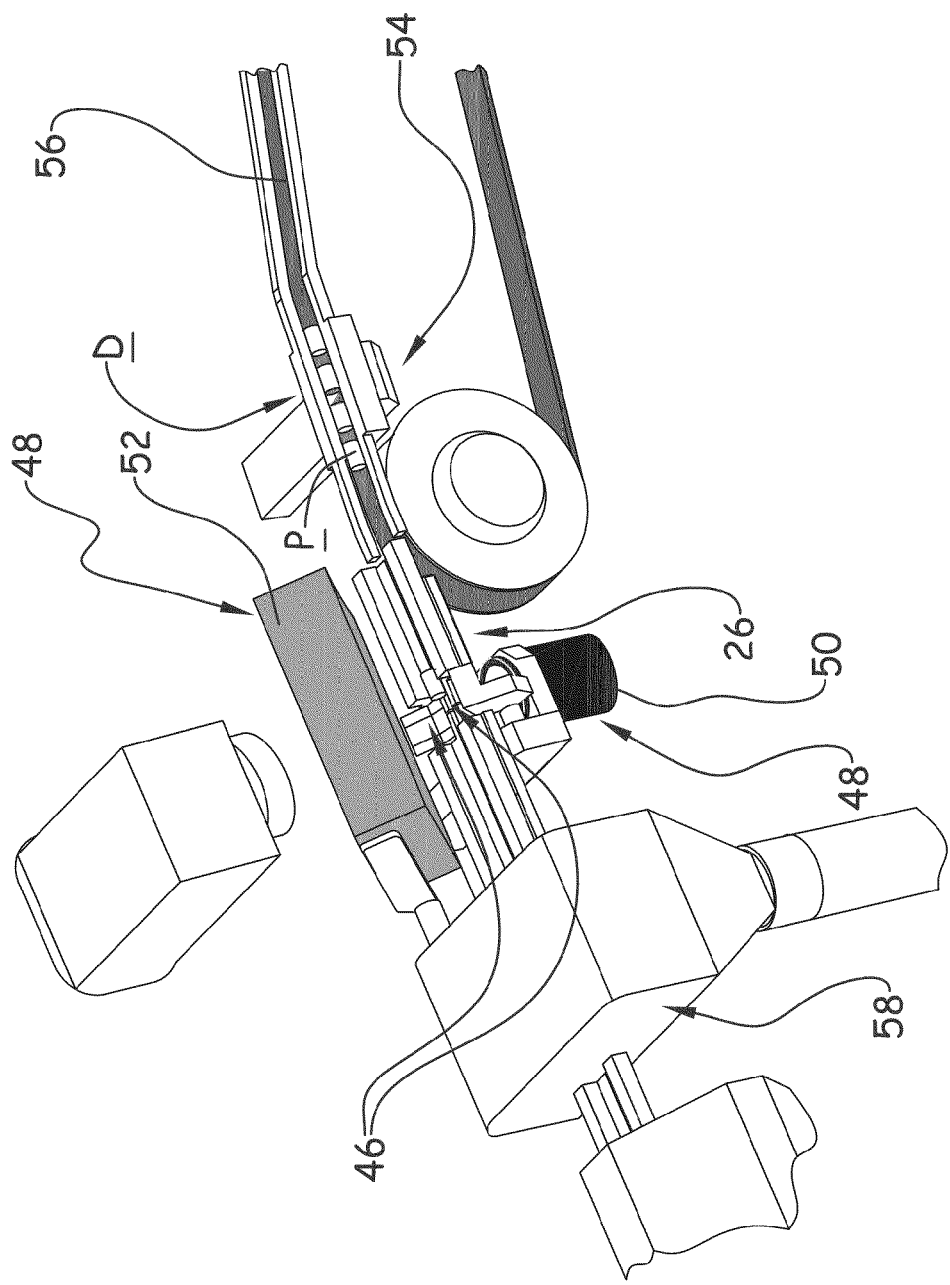
Figure 8:
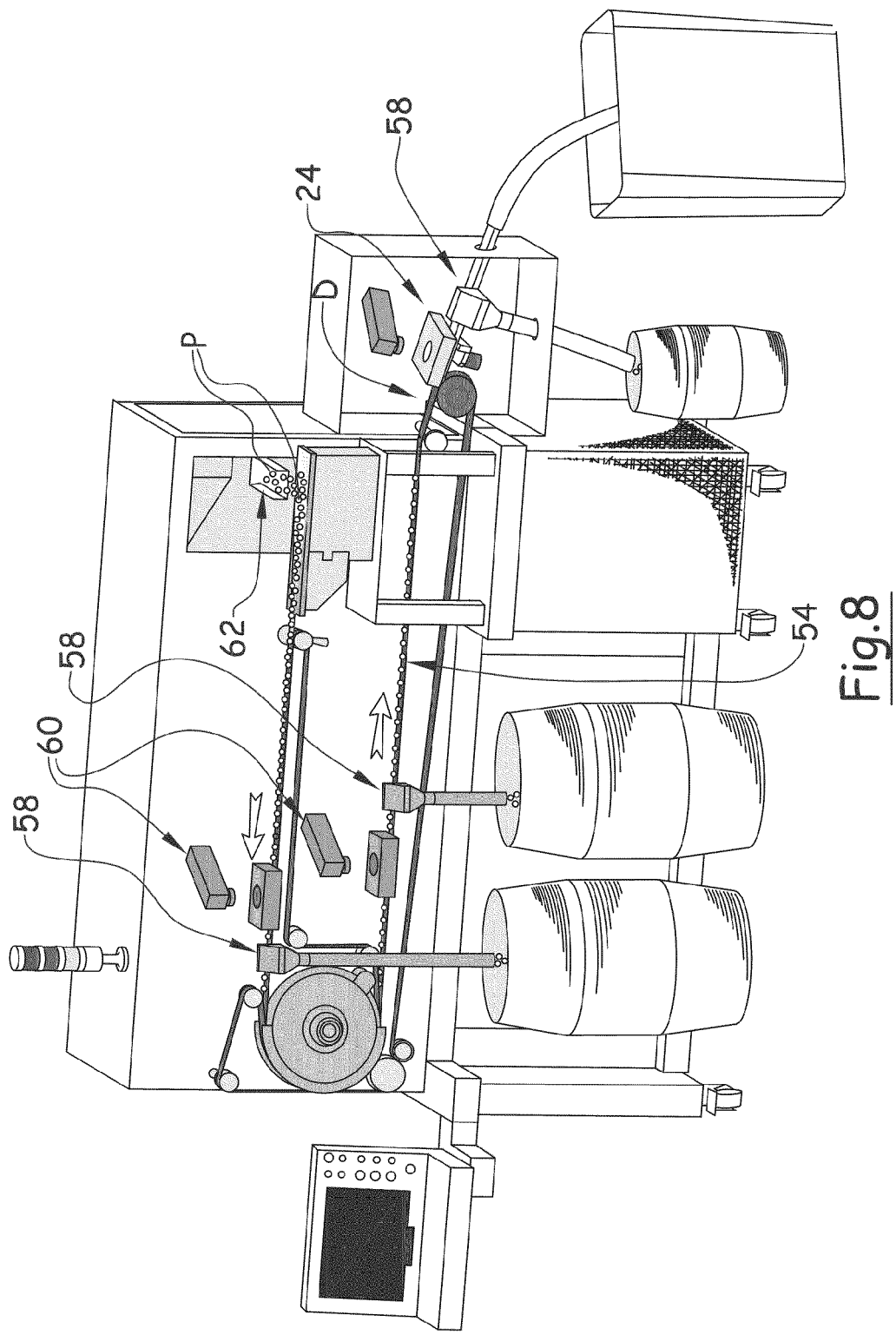

Other characteristics and advantages will emerge from the following description of the invention, a description that is provided only by way of example, with regard to the accompanying drawings in which:

FIG. 1 is a representation of a product P that is to be monitored,

FIGS. 2A and 2B are schematic representations of a first and a second design of an automated visual monitoring device according to the prior art, FIGS. 3A and 3B are schematic representations of a first embodiment of an automated visual monitoring device according to the invention, FIG. 4 is a schematic representation of a second embodiment of an automated visual monitoring device according to the invention, FIG. 5 is a schematic representation of a third embodiment of an automated visual monitoring device according to the invention, FIG. 6 is a detail view of an automated visual monitoring device according to a preferred embodiment of the invention, FIG. 7 is a general view of an automated visual monitoring device according to a preferred embodiment of the invention, FIG. 8 is a view of a production monitoring station that integrates an automated visual monitoring device according to the invention.

As illustrated in FIG. 1, the invention relates to a device 24 for automated visual monitoring of products P that have an elongated shape, i.e., at least as long as wide, having at least one longitudinal axis 10 that is central.

The longitudinal axis 10 is called central because it passes essentially in the center of any section made in said product P of elongated shape.

The automated visual monitoring device 24 that will now be described is more particularly suitable for the inspection of the entire outside longitudinal wall 12 of the products P, i.e., the wall that connects the two surfaces 14 that are located at each end 16 of a product P.

More particularly, the automated visual monitoring device 24 makes possible the monitoring of products P that advance essentially continuously in a direction A, illustrated by an arrow in FIG. 3A, essentially parallel to their longitudinal axis 10.

However, the invention also covers the uses of the automated visual monitoring device for the inspection of products that have different shapes or for the inspection of one or more other walls or surfaces of products that advance in any direction of advance.

Each surface 14 that is located at one of the ends 16 of a product P can be flat, bent, hemispherical, hollow or any other shape.

The inspection of said surfaces 14 located at the ends of a product P with an elongated shape can be easily used by a production monitoring station integrating an automated visual monitoring device 24 according to the invention and making possible inspections in series of said surfaces 14, and the longitudinal wall 12 of the products P is provided at the end of the description.

As illustrated in FIGS. 3A and 3B, an automated visual monitoring device 24 according to this invention comprises guiding means 26 that keep the products P during their passage in the field C of visual monitoring means 28, whereby said field C is indicated in broken lines in the figures.

Said guiding means 26 keep the products P essentially immobile during the visual monitoring so as to ensure the reliability of said monitoring.

These visual monitoring means 28 can use various technologies that make possible the capturing of images of the products P; however, they absolutely must be able to adapt to production rates that are higher than 30 products P to be inspected per second, to provide a connection.

Due to the application of said automated visual monitoring device 24 to products P that advance in their field C of vision, the visual monitoring means 28 comprise at least one linear camera 30. This type of camera, which can have high performance levels and great adaptation possibilities, is particularly suitable to the monitoring of the production of objects, such as the products P, by advance into the field of vision thereof.

According to a preferred embodiment of the automated visual monitoring device 24 according to the invention, and in particular using the design of the guiding means 26 that are associated with at least one reflective surface 32 that is arranged in the field of vision of the visual monitoring means 28 behind the site of passage of the products P, a single linear camera is used for the inspection of the entire outside longitudinal wall 12 of said products P. The image capture means are thus reduced to a minimum relative to the devices of the prior art.

So as to process the images that are captured by a linear camera or any other means of image capture, and therefore to carry out the monitoring of the products P, the visual monitoring means 28 also comprise treatment means connected to said image capture means. These means for processing captured images, making possible the automation of the visual monitoring by filtering, can be carried out in particular from DSP (Digital Signal Processor) accompanied in general by converters and/or adaptors of the transmitted signal. The DSP are particularly suitable for filtering and digital processing operations in real time of the signal that is provided by image capture means.

So as to use only a single camera 30, the guiding means 26 comprise at least one slot 34 that is aligned with at least one reflective surface 32 arranged in the field C of visual monitoring means 28 behind the site of passage of the products P. Said slot 34 makes it possible for the hidden portion of the products P to be reflected by the reflective surface 32 during the passage of said products P above the slot 34.

The hidden portion of the products P is defined as the portion of the outside longitudinal wall 12 of said products P that the visual monitoring means 28 cannot see directly or precisely enough in their field of vision C during their passage.

The slot 34 is a partial or total recess of the guiding means 26 over a distance d that is located in the direction A of advance of the products P. Said distance d is essentially less than the length of the outside longitudinal wall 12 of the products P to be inspected. The slot 34, from a distance d of several millimeters to provide an order of magnitude, makes it possible for the hidden portion of the products P to be reflected on the reflective surface 32 and therefore for an image of said hidden portion of the products P to be captured by the visual monitoring means 28.

For this purpose, said reflective surface 32, at least one, is arranged in the field of the visual monitoring means 28 and preferably essentially oriented facing said visual monitoring means.

The guiding means 26 of the products P, which have an elongated shape and have at least one longitudinal axis 10, preferably come in the form of a slide 36 that comprises at least two guide faces 38 essentially tilted in V shapes, one facing the other.

Said guide faces 38 are essentially symmetrical relative to a longitudinal median plane M, whereby said plane M intersects the field C of the visual monitoring means 28 in its center and is essentially parallel to the direction of advance A of the products P. The guide faces 38 have dimensions and slopes that are suitable for guiding and holding products P to be inspected during their passage in the field C.

According to a preferred embodiment of the automated visual monitoring device 24 that is illustrated in FIG. 6, the slide 36 is machined directly in the mass of the guiding means 26, in particular made of steel, just like the side flanges 40. Said side flanges 40 make it possible simply to prevent a product P that has accidentally left the slide 36 from escaping from said guiding means 26.

So as to ensure the advance of the products P to be inspected, the guiding means 26 are preferably essentially tilted relative to the horizontal line, their lowest end being located obviously on the side toward which it is desired to advance said products P. So as to promote the sliding of the products P, the guide faces 38 have a surface condition that makes it possible to limit and even to eliminate the friction with said products P in movement.

According to a first embodiment, illustrated in FIGS. 3A and 3B, of an automated visual monitoring device 24 according to the invention, so as to make it possible for visual monitoring means 28 to inspect the entire outside longitudinal wall 12 of the products P during their passage in their field C, at least one reflective surface 32 with a straight, concave or convex profile is aligned with at least one slot 34 and arranged in said field C behind the site of passage of said products P.

In this first embodiment, the inspection of a product P is therefore carried out from three views of said product: a direct view of said product and two indirect views of the hidden portion of said product, whereby said indirect views are reflected on both sides of said product by the reflective surface 32. This first embodiment of the device according to the invention therefore makes it possible to obtain an inspection of the product P from three views captured by a single linear camera.

According to a second embodiment, illustrated diagrammatically in FIG. 4, of an automated visual monitoring device 24 according to the invention, at least one slot 34 of the guiding means 26 is aligned with at least two planar surfaces 42 of the reflective surface 32 that are arranged in the field C of the visual monitoring means 28 behind the site of passage of the products P. Said planar surfaces 42 are essentially tilted, one facing the other and oriented so as to reflect a suitable image from the hidden portion of the outside longitudinal wall 12 of the products P toward the visual monitoring means 28.

In this second embodiment, the inspection of a product P is carried out from at least three views of said product: a direct view of said product and at least two indirect views of the hidden portion of said product, whereby said indirect views are reflected on both sides of said product by at least two planar surfaces 42 of the reflective surface 32. This second embodiment of the device according to the invention therefore makes it possible to obtain an inspection of the product P from at least three views that are captured by a single linear camera.

According to a third preferred embodiment, illustrated diagrammatically in FIG. 5 and in more detail in FIG. 6, of an automated visual monitoring device 24 according to the invention, at least one slot 34 of the guiding means 26 is aligned with at least four planar surfaces 42 of the reflective surface 32 that are arranged behind the products P in the field C of the visual monitoring means 28. In this optimized embodiment, said planar surfaces 42 are essentially tilted relative to one another so as to reflect an even more precise image of the hidden portion of the outside longitudinal wall 12 of the products P toward the visual monitoring means 28.

In this third preferred embodiment, the inspection of a product P is carried out from at least five views of said product: a direct view of said product and at least four indirect views of the hidden portion of said product, whereby said indirect views are reflected on both sides of said product by at least four planar surfaces 42 of the reflective surface 32. This third embodiment of the device according to the invention therefore makes it possible to obtain an inspection of the product P from at least five views that are captured by a single linear camera, thus considerably improving the quality and the reliability of the automated visual monitoring device 24.

Still according to a preferred embodiment of the automated visual monitoring device 24, the four planar surfaces 42 of the reflective surface 32 are arranged essentially symmetrically on both sides of the longitudinal median plane M. Thus, from each side of said plane M, two contiguous planar surfaces (42-1, 42-2) are tilted respectively by an angle ($\alpha$, $\beta$) relative to the horizontal. A detachable support 44 is provided to allow an easy change of said planar surfaces 42 and more particularly so to easily modify their respective angle of inclination ($\alpha$, $\beta$) and/or their respective positioning relative to the products P and to the visual monitoring means 28.

So as to carry out, under the best possible conditions, the inspection of the hidden portion of the products P, in its preferred embodiment, an automated visual monitoring device 24 uses guiding means 26 with lateral releases 46 of material on both sides of said slot 34 as well as lighting means 48 that are suitable for the monitoring process and for the desired defect types.

Said lateral releases 46 of material, illustrated in FIG. 7, make possible the optimization of the lighting of the products P that pass at the level of the slot 34, but they also allow a closer positioning of the planar surfaces 42 of the reflective surface 32 so as to improve the images that are reflected and therefore captured by the visual monitoring means 28.

According to the monitored defect type, the lighting means 48 can provide lighting with different characteristics.

Thus, for the detection of black spots, impressions, color variations or deposits on the products P to be monitored, a diffuse lighting will preferably be selected. This diffuse lighting can be implemented, for example, as illustrated in FIGS. 6 and 7, from a first light source 50 and a second light source 52, or else from a circular lighting obtained using at least one LED ring.

In the case of the detection of irregular coatings, chips or cracks on the products P to be monitored, a low-angled lighting will preferably be selected.

So as to bring the products P to be monitored on the guiding means 26, an automated visual monitoring device 24 can integrate conveying means 54 with a rabbeted band 56 of the products P in an essentially horizontal position, whereby said conveying means 54 are located, of course, upstream from said guiding means 26.

In a preferred embodiment of the invention, so as to increase the rate of inspection of the products P, in particular higher than 30 products P per second, the tilting of the guiding means 26 relative to the horizontal can be increased to promote a higher speed of advance of the products P to be inspected. So as to ensure a transition between their essentially horizontal position on the conveying means 54 and their tilted position of advance on very tilted guiding means 26, said conveying means 54 have at least one downflowing portion D located at their end just upstream from said guiding means 26, whereby said portion D has an intermediate slope that is comparable to the slope of the guiding means 26 relative to the conveying means 54. This downflowing transition portion D makes it possible to prevent the separation of the products P, separation that would be caused by the intake speed of the products P at the change in slope between the conveying means 54 and the guiding means 26.

In an improved embodiment, this downflowing portion D of the conveying means 54 can integrate intake means that make it possible to further increase the speed of advance of the products P without separation.

Advantageously, said intake means that are integrated with said portion D can even make it possible to homogenize and to monitor the speed of advance of the products P on the guiding means 26 and therefore their speed of passage in the field C of the visual monitoring means 28.

After the monitoring of a product P and in the case where said product has one or more defects that are detected by the processing means of the visual monitoring means 28, the automated visual monitoring device according to the invention comprises means 58 for rejecting defective products P, located downstream from the slot 34 of the guiding means 26 and controlled by the processing means of the visual monitoring means 28.

These rejection means 58 can consist of means of compressed air expulsion, such as a small bellows, or any other mechanical expulsion means, such as a retractable pin. In addition, whereby the products P are able to advance at very high speeds, so as to expel selectively and precisely a defective product, the visual monitoring means 28 estimate the sliding speed of each product P for a precise triggering of the rejection means 58. For example, too significant a variation of the speed of advance of a product P can be considered to be a rejection criterion.

FIG. 8 shows a production monitoring station that integrates an automated visual monitoring device 24 according to the invention so as to conduct inspections in series of the surfaces 14 and the outside longitudinal wall 12 of products P of elongated shape. In this connection, said production monitoring station also integrates two visual monitoring devices 60 of said surfaces 14 that are known to one skilled in the art.

The products P to be monitored are deposited by supply means 62 on the rabbeted belt 56 of the conveying means 54 of the device 24 according to the invention and are monitored successively by the visual monitoring devices 60 of said surfaces 14 and then by the automated visual monitoring device 24 according to the invention, whereby rejection means 58 are also provided between the visual monitoring devices 60 and the automated visual monitoring device 24.

It is noted that the device 24 according to the invention makes it possible to limit to only three cameras the number of image capture means that is necessary to ensure the inspection of the entire outside periphery of the products P of elongated shape. Such a device is more advantageous in terms of maintenance and production cost compared to the devices of the prior art.

The invention claimed is:

1. Device (24) for automated visual monitoring of products P, in particular products of elongated shape, having at least one longitudinal axis (10) and advancing essentially continuously in a direction A that is essentially parallel to their longitudinal axis (10), whereby said device (24) comprises guiding means (26), automated visual monitoring means (24), and at least one reflective surface (32), whereby said guiding means (26) keep the products P during their passage in the field C by means of visual monitoring (28), said automated visual monitoring device (24) is characterized in that the guiding means (26), keeping the products P essentially immobile during the visual monitoring, comprise at least one slot (34) that is aligned with at least one reflective surface (32) that is arranged in the field C of the visual monitoring means (28) behind the site of passage of the products P.

2. Device (24) for automated visual monitoring (24) of the products P according to claim 1, wherein the visual monitoring means (28) comprise a single linear camera (30) for the inspection of the entire outside longitudinal wall (12) of the products P.

3. Device (24) for automated visual monitoring of the products P according to claim 2, wherein at least one reflective surface (32) has a concave or convex profile.

4. Device (24) for automated visual monitoring of products P according to claim 2, wherein at least one slot (34) of the guiding means (26) is aligned with at least two planar surfaces (42) of the reflective surface (32) arranged in the field C of the visual monitoring means (28) behind the site of passage of the products P, whereby said planar surfaces (42) are essentially tilted facing one another.

5. Device (24) for automated visual monitoring of products P according to claim 2, wherein at least one slot (34) of the guiding means (26) is aligned with at least four planar surfaces (42) of the reflective surface (32) arranged behind the products P in the field C of the visual monitoring means (28), and whereby said planar surfaces (42) are essentially tilted relative to one another.

6. Device (24) for automated visual monitoring of products P according to claim 2, wherein the guiding means (26) are essentially tilted relative to the horizontal.

7. Device for automated visual monitoring of products P according to claim 2, wherein the guiding means (26) come in the form of a slide (36) that comprises at least two guide faces (38) that are tilted facing one another, with dimensions and slopes suitable for the products P.

8. Device (24) for automated visual monitoring (24) of products P according to claim 2, whereby said automated visual monitoring device (24) integrates means (54) for conveying, with a rabbeted belt (56), products P that are located upstream from the guiding means (26), wherein said conveying means (54) have at least one downflowing portion D that is located at their end just upstream from the guiding means (26), whereby said portion D has an intermediate slope comparable to the slope of the guiding means (26) relative to the conveying means (54).

9. Device (24) for automated visual monitoring of the products P according to claim 1, wherein at least one reflective surface (32) has a concave or convex profile.

10. Device (24) for automated visual monitoring of products P according to claim 1, wherein at least one slot (34) of the guiding means (26) is aligned with at least two planar surfaces (42) of the reflective surface (32) arranged in the field C of the visual monitoring means (28) behind the site of passage of the products P, whereby said planar surfaces (42) are essentially tilted facing one another.

11. Device (24) for automated visual monitoring of products P according to claim 1, wherein at least one slot (34) of the guiding means (26) is aligned with at least four planar surfaces (42) of the reflective surface (32) arranged behind the products P in the field C of the visual monitoring means (28), and whereby said planar surfaces (42) are essentially tilted relative to one another.

12. Device (24) for automated visual monitoring of products P according to claim 1, wherein the guiding means (26) are essentially tilted relative to the horizontal.

13. Device for automated visual monitoring of products P according to claim 1, wherein the guiding means (26) come in the form of a slide (36) that comprises at least two guide faces (38) that are tilted facing one another, with dimensions and slopes suitable for the products P.

14. Device (24) for automated visual monitoring (24) of products P according to claim 1, whereby said automated visual monitoring device (24) integrates means (54) for conveying, with a rabbeted belt (56), products P that are located upstream from the guiding means (26), wherein said conveying means (54) have at least one downflowing portion D that is located at their end just upstream from the guiding means (26), whereby said portion D has an intermediate slope comparable to the slope of the guiding means (26) relative to the conveying means (54).

15. Device (24) for automated visual monitoring of products P according to claim 1, wherein it comprises means (58) for rejecting defective products P, located downstream from the slot (34) of the guiding means (26) and controlled by means for processing visual monitoring means (28).

16. Production monitoring station integrating an automated visual monitoring device (24) according to claim 1.

\* \* \* \* \*